US00PP09262P

United States Patent [19]

Meilland

[11] Patent Number: Plant 9,262

[45] Date of Patent: Aug. 29, 1995

[54] HYBRID TEA ROSE PLANT NAMED 'MEISINPLOX'

[75] Inventor: Alain A. Meilland, Antibes, France

[73] Assignee: The Conard-Pyle Company, West Grove, Pa.

[21] Appl. No.: 314,391

[22] Filed: Sep. 28, 1994

[30] Foreign Application Priority Data

Jun. 28, 1994 [FR] France ..... 13527

[51] Int. Cl.[6] ..... A01H 5/00

[52] U.S. Cl. ..... Plt./15

[58] Field of Search ..... Plt. 15, 24

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms attractive intense yellow blossoms that well retain their coloration. Such blossoms are long-lasting when placed in a vase and exhibit good petal-drop characteristics. The plant exhibits an erect growth habit, strong vegetation, and glossy dark green decorative foliage that contrasts well with the intense yellow blossom coloration. Additionally, the plant exhibits excellent disease resistance.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the Meijason variety (U.S. Plant Pat. No. 5,622). The male parent (i.e., the pollen parent) was formed by the cross of the Jacblem variety (non-patented in the United States) and the Poultex variety (U.S. Plant Pat. No. 6,261). The parentage of the new variety can be summarized as follows:

MEIJASON×(JACBLEM×POULTEX).

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive long-lasting intense yellow blossoms that well retain their coloration, (b) exhibits an erect growth habit with glossy dark green decorative foliage that contrasts well with the intense yellow blossom coloration, (c) is well susceptible to forcing, and (f) exhibits excellent disease resistance.

The new Hybrid Tea rose plant of the present invention responds well to greenhouse forcing and to cold culture conditions.

The new variety well meets the needs of the horticultural industry and is particularly well suited for cut flower production in greenhouses.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the Meisinplox variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during June while budded on *Rosa indica* understock and growing in greenhouses at Le Cannet des Maures, Var, France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of an open flower — plan view — obverse;

FIG. 7 — illustrates a specimen of an open flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates specimens of a leaf with five leaflets — plan view — under surface; and FIG. 16 — illustrates a specimen of a leaf with seven leaflets — plan view — upper surface.

DETAILED DESCRIPTION

Figures 1, 2, 3, 4, 5, 6, 7, 8, 9, 10, 11, 12, 13, 14, 15, 16:
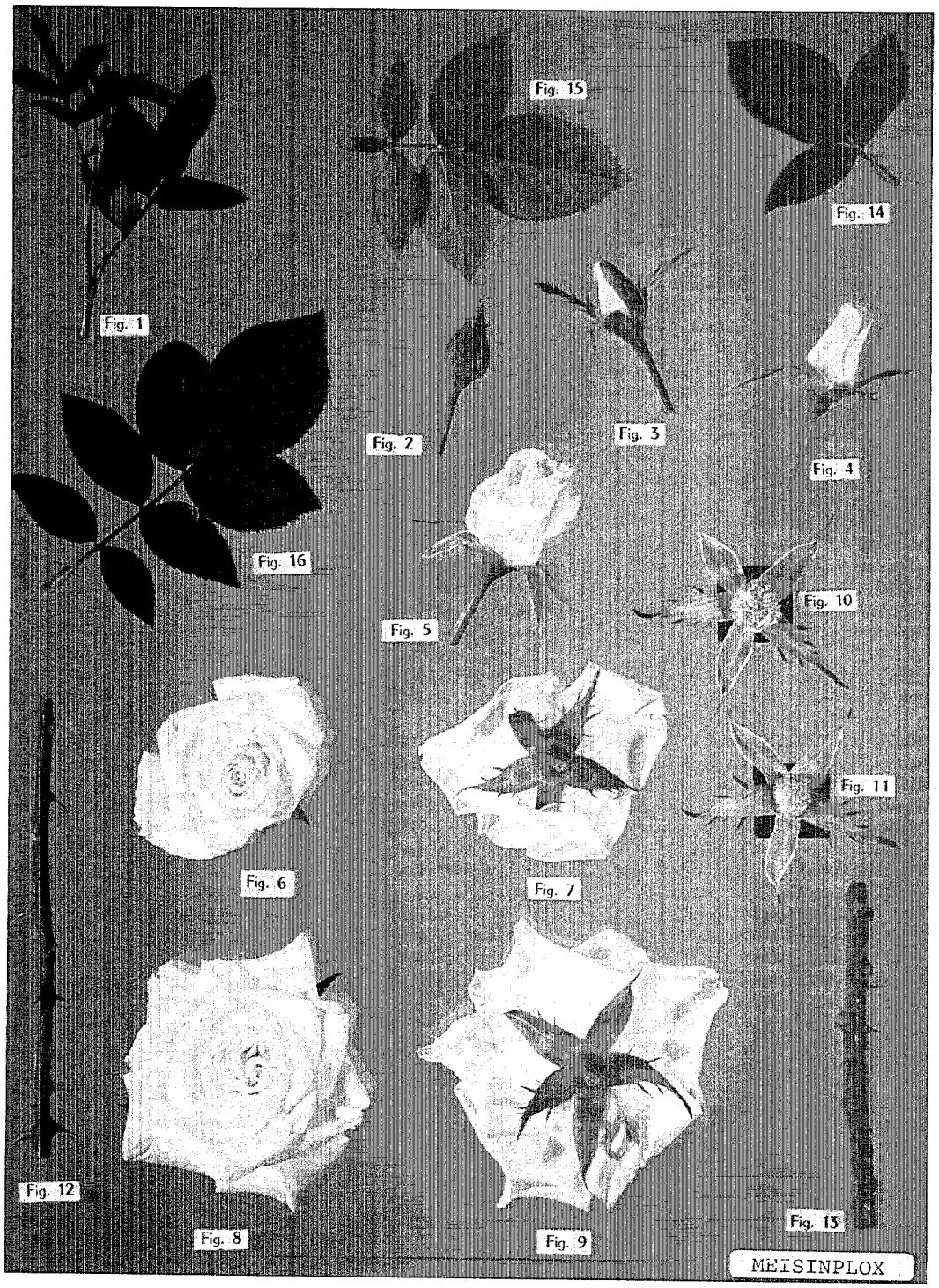

The chart used in the identification of the colors is that of The Royal Horticultural Society (R.H.S. Colour Chart). The description is based on the observation of two year-old plants while budded on *Rosa indica* understock and growing in greenhouses at Le Cannet des Maures, Var, France. The coloration in common terms precedes reference to the chart.

Class: Hybrid Tea.

Plant:

*Height.*—Approximately 50 to 80 cm. on average at the end of the growing season.

*Habit.*—Erect.

Branches:

*Color.*—Young stems: medium green, Green Group 137A, and more or less suffused with reddish brown. Adult wood: medium green, Green Group 137A.

*Thorns.*—Size: medium. Quantity: moderately numerous. Color: reddish on young stems and greenish on adult wood.

Leaves:

*Stipules.*—Adnate, pectinate, wide, and linear.

*Petioles.*—Upper surface: striped reddish brown on young foliage and medium green on adult foliage with more or less glandular edges. Under surface: light green and bear some small prickles.

*Leaflets.*—Number: 3, 5, and 7 (most often), and sometimes the first pair of leaves is incomplete. Shape: elliptic. Serration: single and regular. Texture: consistent. General appearance: dense, dark green, and bright. Color (young foliage): upper surface: reddish-brown. under surface: reddish-brown. Color (adult foliage): upper surface: dark green, Green Group 139A, and suffused with medium green, Green Group 137A. under surface: grey green, Greyed-Green Group 191A.

Inflorescence

*Number of flowers.*—Usually one per stem.

*Peduncle.*—Medium green and smooth. The length is approximately 11 to 13 cm. on average.

*Sepals.*—Upper surface: tomentose, and greenish in coloration. Under surface: light green in coloration with more or less small appendiculated edges.

*Buds.*—Shape: conical. Length: approximately 4 cm. on average. Size: large. Color upon opening: under surface: Lemon Yellow, Yellow-Orange Group 14B. under surface: Lemon Yellow, Yellow Group 13B.

*Flower.*—Shape: cup-shaped. Diameter: approximately 14 cm. on average. Color (when opening begins): upper surface: Naples Yellow, Yellow Group 11A. under surface: Naples Yellow, Yellow Group 11A. Color (when blooming): upper surface: Naples Yellow, Yellow Group 11A. under surface: Naples Yellow, Yellow Group 11A. Color (at end of opening): upper surface: Naples Yellow, Yellow Group 11A. under surface: Naples Yellow, Young Group 11A. Fragrance: none. Lasting quality: long when cut and placed in vase. Petal number: approximately 35 on average. Petal shape: flatly rounded with cordate-shaped base. Petal drop: good. Stamen number: approximately 224 on average. Anthers: normal and golden yellow in coloration with ochre coloration at tip. Filaments: yellow in coloration with fuchsia tips, and commonly of irregular heights. Pistils: approximately 112 on average. Stigmas: normal, and strawlike. Styles: greenish in coloration, commonly twisted, and tomentose at base. Receptacle: medium green, smooth, and in longitudinal section in the shape of a wide funnel.

Development:

*Vegetation,.*—Strong.

*Blooming.*—Abundant.

*Resistance to diseases.*—Excellent.

I claim:

1. A new and distinct variety of Hybrid Tea rose plant characterized by the following combination of characteristics:

(a) forms in abundance attractive long-lasting intense yellow blossoms that well retain their coloration, (b) exhibits an erect growth habit with glossy dark green decorative foliage that contrasts well with the intense yellow blossom coloration, (c) is well susceptible to forcing, and (d) exhibits excellent disease resistance;

substantially as herein shown and described.

* * * * *

METSINPLOX